(12) United States Patent
Venegas

(10) Patent No.: US 10,926,053 B2
(45) Date of Patent: Feb. 23, 2021

(54) CLOSED-CIRCUIT BREATHING DEVICE

(71) Applicant: THE GENERAL HOSPITAL CORPORATION, Boston, MA (US)

(72) Inventor: Jose G. Venegas, Boston, MA (US)

(73) Assignee: The General Hospital Corporation, Boston, MA (US)

(*) Notice: Subject to any disclaimer, the term of this patent is extended or adjusted under 35 U.S.C. 154(b) by 695 days.

(21) Appl. No.: 15/528,942

(22) PCT Filed: Nov. 20, 2015

(86) PCT No.: PCT/US2015/061835
§ 371 (c)(1),
(2) Date: May 23, 2017

(87) PCT Pub. No.: WO2016/085807
PCT Pub. Date: Jun. 2, 2016

(65) Prior Publication Data
US 2017/0259023 A1 Sep. 14, 2017

Related U.S. Application Data

(60) Provisional application No. 62/084,310, filed on Nov. 25, 2014.

(51) Int. Cl.
*A61M 16/08* (2006.01)
*A61M 16/20* (2006.01)
(Continued)

(52) U.S. Cl.
CPC ........ *A61M 16/0891* (2014.02); *A61M 16/12* (2013.01); *A61M 16/201* (2014.02);
(Continued)

(58) Field of Classification Search
CPC ......... A61B 5/082; A61B 5/083; A61B 5/091; A61B 17/32; A61B 17/1322;
(Continued)

(56) References Cited

U.S. PATENT DOCUMENTS 2,354,452 A   7/1944  Foregger
4,020,834 A * 5/1977  Bird ..................... A61M 16/00
                                                    128/204.25

(Continued)

OTHER PUBLICATIONS

Bruce H. Culver, in Clinical Respiratory Medicine (Fourth Edition), 2012 by Stephen G. Spiro, Gerard A. Silvestri and Alvar Agustí, pp. 133-142 (Year: 2012).*

(Continued)

*Primary Examiner* — Joseph D. Boecker
*Assistant Examiner* — Thomas W Greig
(74) *Attorney, Agent, or Firm* — Quarles & Brady LLP

(57) ABSTRACT

Described here are closed-circuit breathing devices and methods for their use. In general, the closed-circuit breathing device is configured to achieve a steady-state equilibrium, whereby therapeutic gas is introduced into the breathing circuit in small, controlled volumes until a steady state concentration of the therapeutic gas is reached. During this time, the closed-circuit breathing device is operated in a true closed circuit, such that the therapeutic gas is not lost to the atmosphere. Safety measures are built into the closed-circuit breathing device so that a hypoxic mixture is not delivered to the subject. The therapeutic gas may be xenon.

22 Claims, 3 Drawing Sheets

(51) Int. Cl.
*A61M 16/22* (2006.01)
*A61M 16/12* (2006.01)
*A61M 16/00* (2006.01)

(52) U.S. Cl.
CPC ........ *A61M 16/202* (2014.02); *A61M 16/208* (2013.01); *A61M 16/22* (2013.01); *A61M 16/0078* (2013.01); *A61M 2016/003* (2013.01); *A61M 2016/0042* (2013.01); *A61M 2202/0208* (2013.01); *A61M 2202/0291* (2013.01); *A61M 2205/505* (2013.01); *A61M 2230/432* (2013.01); *A61M 2230/435* (2013.01); *A61M 2230/437* (2013.01)

(58) Field of Classification Search
CPC ........ A61B 17/1325; A61B 2562/0219; A61B 5/003; A61B 5/055; A61B 5/0833; A61B 5/0836; A61B 5/087; A61B 5/412; A61B 5/4821; A61B 5/4836; A61B 5/7207; A61B 90/00; A41D 13/0512; G01R 33/5601; G01R 33/56366; Y10S 128/911; Y10S 128/914; A61F 5/05883; A61F 5/30; A61K 31/07; A61K 31/573; A61K 31/65; A61M 16/0003; A61M 16/0045; A61M 16/0057; A61M 16/0066; A61M 16/0069; A61M 16/0081; A61M 16/024; A61M 16/026; A61M 16/04; A61M 16/0488; A61M 16/049; A61M 16/06; A61M 16/0605; A61M 16/0616; A61M 16/0633; A61M 16/0666; A61M 16/0683; A61M 16/0694; A61M 16/08; A61M 16/0833; A61M 16/0875; A61M 16/1045; A61M 16/1055; A61M 16/1065; A61M 16/107; A61M 16/12; A61M 16/125; A61M 16/16; A61M 16/20; A61M 16/202; A61M 16/204; A61M 16/205; A61M 16/206; A61M 16/208; A61M 16/209; A61M 16/22; A61M 2016/0027; A61M 2016/003; A61M 2016/0036; A61M 2016/0039; A61M 2016/0413; A61M 2016/103; A61M 2202/0007; A61M 2202/0014; A61M 2202/0208; A61M 2202/0225; A61M 2205/3313; A61M 2205/3334; A61M 2205/3365; A61M 2205/36; A61M 2205/502; A61M 2205/52; A61M 2205/82; A61M 2210/0625; A61M 2230/00; A61M 2230/005; A61M 2230/04; A61M 2230/202; A61M 2230/205; A61M 2230/208; A61M 2230/40; A61M 2230/432; A61M 2230/435; A61M 2230/437; A61M 16/01; A61M 16/0891; A61M 16/201

See application file for complete search history.

(56) References Cited

U.S. PATENT DOCUMENTS

| | | | | |
|---|---|---|---|---|
| 4,233,842 | A * | 11/1980 | Raemer | A61B 5/083 600/532 |
| 4,267,827 | A * | 5/1981 | Rauscher | A61B 5/0813 128/205.15 |
| 4,622,976 | A * | 11/1986 | Timpe | A61B 5/0275 128/203.14 |
| 4,764,346 | A * | 8/1988 | Lewis | A61M 16/0057 128/204.28 |
| 4,779,621 | A * | 10/1988 | Mattson | A61B 5/0813 378/18 |
| 4,938,212 | A * | 7/1990 | Snook | A61M 16/0677 128/205.24 |
| 5,197,481 | A * | 3/1993 | Fisher | A61B 5/0836 600/532 |
| 5,651,360 | A * | 7/1997 | Tobia | A61M 16/209 128/204.28 |
| 6,095,137 | A * | 8/2000 | Wallroth | A61M 16/01 128/203.26 |
| 6,135,107 | A * | 10/2000 | Mault | A61B 5/0836 128/204.23 |
| 6,148,816 | A * | 11/2000 | Heinonen | A61M 16/204 128/205.24 |
| 6,220,244 | B1 * | 4/2001 | McLaughlin | A61M 16/0051 128/204.23 |
| 6,254,546 | B1 * | 7/2001 | Vierto-Oja | A61B 5/0813 600/529 |
| 6,955,652 | B1 * | 10/2005 | Baum | A61B 5/0813 600/529 |
| 8,128,574 | B2 * | 3/2012 | Baker, Jr. | A61B 5/0836 600/529 |
| 2005/0028816 | A1 * | 2/2005 | Fishman | A61M 16/0051 128/200.24 |
| 2005/0045180 | A1 | 3/2005 | Heinonen | |
| 2007/0062532 | A1 * | 3/2007 | Choncholas | A61M 16/024 128/204.23 |
| 2008/0289628 | A1 * | 11/2008 | Hallback | A61B 5/0813 128/203.12 |
| 2009/0050148 | A1 | 2/2009 | Heinonen et al. | |
| 2009/0137919 | A1 * | 5/2009 | Bar-Lavie | A61B 5/0833 600/538 |
| 2009/0320844 | A1 * | 12/2009 | Nielsen | A61B 5/029 128/204.22 |
| 2011/0315139 | A1 * | 12/2011 | Mashak | A61M 16/209 128/203.14 |
| 2013/0261487 | A1 | 10/2013 | Baker, Jr. et al. | |
| 2014/0238398 | A1 | 8/2014 | Christopher et al. | |

OTHER PUBLICATIONS

Ravishankar et al., Inhalational Anaesthesia, Aug. 11, 2013, Suvarna JNMC Anaesthesia, pp. 1-85 [online]. [retrieved on Mar. 24, 2020]. Retrieved from the Internet <URL: https://www.slideshare.net/ashwinhgtx/inahalational-anaesthesia>.*

International Search Report and Written Opinion for International Application No. PCT/US15/61835 dated Mar. 25, 2016.

* cited by examiner

CLOSED-CIRCUIT BREATHING DEVICE

CROSS-REFERENCE TO RELATED APPLICATIONS

This application represents the U.S. National Stage of International Application No. PCT/US2015/061835, filed Nov. 20, 2015 which is based on, claims priority to, and incorporates herein by reference in its entirety, U.S. Provisional Application Ser. No. 62/084,310, filed Nov. 25, 2014, and entitled "Closed-Circuit Breathing Device."

BACKGROUND

The present disclosure relates to systems and methods for providing a therapeutic agent to a subject for inhalation. More particularly, disclosure relates to systems and methods for closed-loop breathing circuits.

Anxiety and addiction disorders, including Post Traumatic Stress Disorder ("PTSD"), Obsessive Compulsive Disorder ("OCD"), and addiction disorders are associated with tremendous personal and societal burdens. These and several other disorders that could benefit from xenon therapy, argon therapy, or both, are undertreated and collectively cost the US over $1 Trillion annually. Specifically, for PTSD and OCD, behavioral therapy is often ineffective with 40% to 50% of the patients being nonresponders. Pharmacotherapies, including antidepressant medications, are also prescribed but are effective in only about 25%-60% of the patients.

Xenon is a rare, expensive gas with remarkable therapeutic potential that has yet to be realized. The gas is used clinically to a very limited extent as an anesthetic and a diagnostic imaging agent, and in those applications it exhibits excellent safety and side-effect profiles, meaning that it is a prime candidate for repurposing.

The therapeutic use of xenon is supported by strong theoretical foundations documenting its effects on biological targets that play critical roles in anxiety. Emotional memory abnormalities also play key roles in OCD and addiction disorders and, thus, it is contemplated that xenon will effectively treat these disorders. There is substantial human experience using xenon at high and low concentrations as an anesthetic and a diagnostic imaging agent, respectively. In these applications, xenon has excellent safety and side-effect profiles. Thus, xenon is already at an advanced stage in the therapeutic development process. However, to realize any of the many potential therapeutic uses of xenon, a cost effective device to deliver the gas is required.

A major impediment to the clinical use of xenon as a therapeutic agent is the lack of proper delivery systems. Commercial devices to deliver xenon as an anesthetic agent, or as a contrast media for CT, exist; however, these devices are expensive, require supervision of specialized personnel, and were not designed to optimize the use of the very expensive gas.

While other methods exist to administer xenon—including intraocularly via pressure fitting goggles, intranasally, and via intravenous administration of stable liposomal preparations containing xenon—the most practical means to administer xenon is via an easy to use breathing device. Advancing the therapeutic uses of xenon therefore requires a delivery device that is safe, cost effective, and that can be used by spontaneously breathing subjects with minimal supervision.

SUMMARY

The present disclosure overcomes the aforementioned drawbacks by providing closed-circuit breathing devices and methods for their use. In general, the closed-circuit breathing devices can be configured to rapidly achieve a steady-state equilibrium, whereby a therapeutic gas, such as xenon, is introduced into the breathing circuit of the device in incremental, controlled volumes until a steady state concentration of the therapeutic gas is reached.

It is an aspect of the disclosure to provide a closed-circuit breathing device that generally includes a breathing port, a breathing circuit, a sensor assembly, a chamber, and a controller. The breathing port and the sensor assembly are both in fluid communication with the breathing circuit. The sensor assembly is configured to measure at least one of a concentration or a flow rate of gases inhaled out and exhaled into the breathing circuit. The chamber is also in fluid communication with the breathing circuit, and is configured to hold a known volume of a pressurized therapeutic gas. The controller is in communication with the sensor assembly and the chamber, and is configured to receive data from the sensor assembly. Based on this received data, the controller is configured to control delivery of the therapeutic gas from the chamber to bring a concentration of the therapeutic gas in the breathing circuit to a predetermined steady-state value.

It is another aspect of the disclosure to provide a method for operating a closed-circuit breathing device having a breathing circuit. The method includes delivering oxygen to the breathing circuit to establish a predetermined concentration of oxygen in the breathing circuit while operating the closed-circuit breathing device in an open configuration. A dead space volume, such as a dead space volume of the subject's airway, is estimated based on carbon dioxide exhaled into the breathing circuit during a washout period while operating the closed-circuit breathing device in an open configuration. In addition, the subject's lung volume is estimated based at least in part on the estimated dead space volume and on nitrogen exhaled into the breathing circuit during a washout period while operating the closed-circuit breathing device in an open configuration. For example, the subject's lung volume can be based in part on the volume of breathing gas and its nitrogen concentration that is exhaled during the washout period. A volume of therapeutic gas to deliver to the breathing circuit is then estimated based at least in part on the estimated lung volume. The closed-circuit breathing device is then controlled to maintain oxygen concentration in the breathing circuit at a steady-state value while raising a concentration of the therapeutic gas in the breathing circuit to a steady-state value while operating the closed-circuit breathing device in a closed configuration. The closed-circuit breathing device is then controlled to maintain the concentration of the therapeutic gas in the breathing circuit at the steady-state value for a treatment period while operating the closed-circuit breathing device in a closed configuration.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
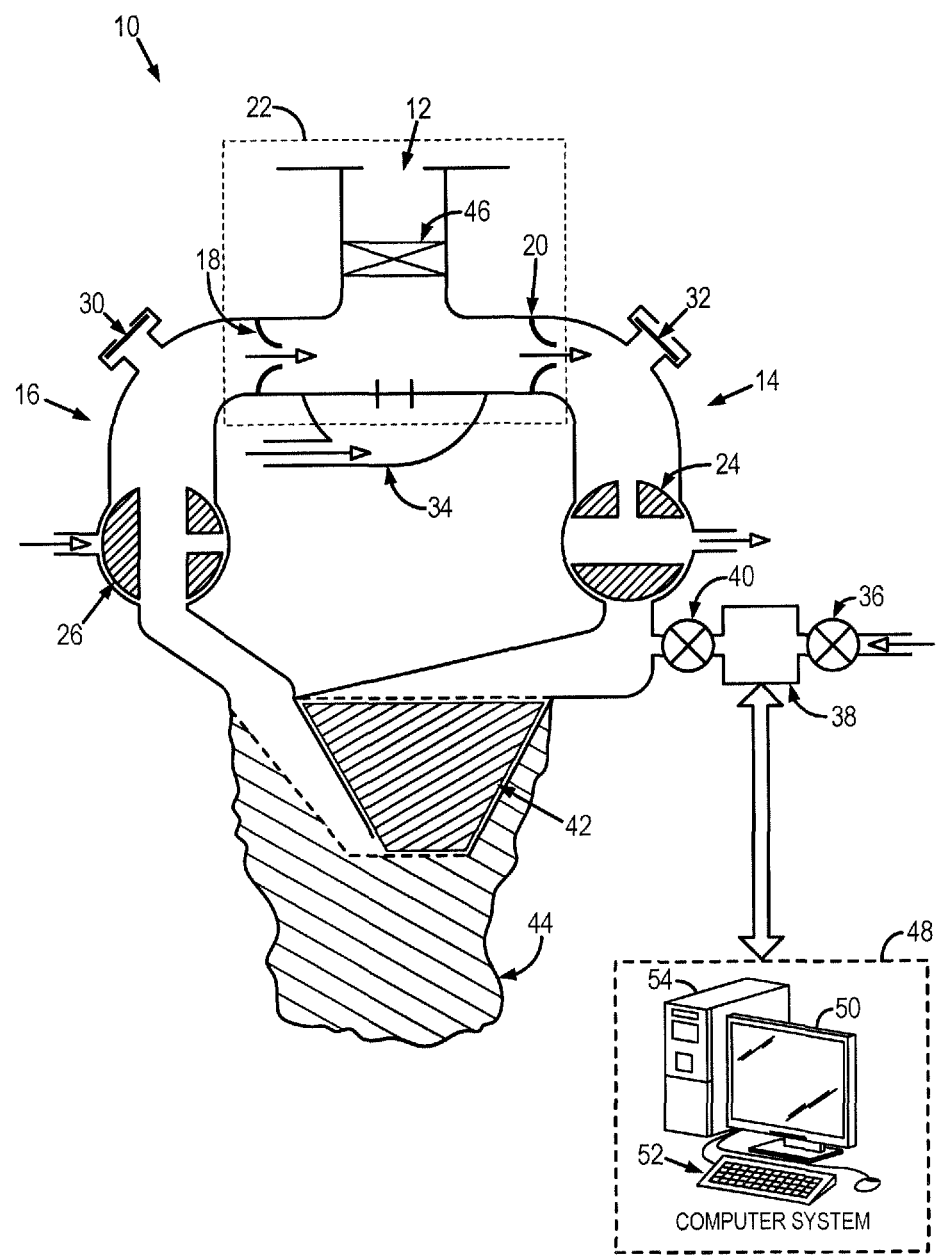
FIG. 1 is an example of a closed-circuit breathing device that can be used for the delivery of a therapeutic gas, such as xenon, to a subject with minimal loss of the therapeutic gas to the atmosphere.

Described here is a closed-circuit breathing device and methods for its use. In general, the closed-circuit breathing device is configured for exposing a subject to predefined concentrations of gas mixtures for uses that include clinical use. As one particular application, the closed-circuit breathing device is useful for administering xenon gas to a subject.

Due to the cost of xenon, the gas must be administered through a, closed-circuit re-breathing system for practical use. The closed-circuit breathing device described here is capable of this functionality. The device described here minimizes wastage of the gas while supplying fresh oxygen and xenon to the breathing circuit as the gases are consumed by the subject. The device safely delivers a controlled xenon-oxygen mixture to the subject.

The closed-circuit breathing device described here is also configured to remove carbon dioxide generated by the subject from the breathing circuit. Also, to reduce the amount of other breathing gases in the system, such as nitrogen, to leave room for the xenon, the device can allow breathing with 100 percent oxygen for a washout period prior to exposure to the defined xenon-oxygen concentration. Transition from breathing oxygen to the xenon-oxygen mixture can be made with minimal, or no, xenon loss.

The closed-circuit breathing device described here provides advantages over existing devices. As will be described below, the closed-circuit breathing device is capable of achieving a steady-state equilibrium, whereby therapeutic gas is introduced into the breathing circuit in small, controlled volumes until a steady state concentration of the therapeutic gas is reached. During this time, the closed-circuit breathing device is operated in a true closed circuit, such that the therapeutic gas is not lost to the atmosphere. Safety measures are built into the closed-circuit breathing device so that a hypoxic mixture is not delivered to the subject.

Typical closed-circuit breathing devices in anesthesia are used in an open or semi-open system to maintain the inspiratory concentration of the agent at a constant therapeutic level until the system reaches a steady state and the exhaled concentration equals that of inhalation. When that steady state is finally reached, the system would be closed. In the closed-circuit breathing devices described here, the volume of therapeutic gas that is needed is estimated and delivered into a closed system that has previously been prepared by washing out the nitrogen in order to make "room" for the therapeutic gas.

As will be described, systems and methods for closed-circuit breathing are provided, which can be useful in a variety of applications. For example, they can be configured to rapidly achieve a steady-state equilibrium, whereby a therapeutic or diagnostic gas, such as xenon, is introduced into the breathing circuit of the device in incremental, controlled volumes until a steady state concentration of the therapeutic gas is reached. The therapeutic or diagnostic gas can include a variety of gases used for various clinical applications, such as anesthetic gases or a gaseous diagnostic imaging agent, to name but a few non-limiting examples. Reference to a particular gas or clinical application hereafter is for exemplary purposes and is non-limiting.

Referring now to FIG. 1, an example of a closed-circuit breathing device 10 in accordance with some configurations of the present disclosure is illustrated. The closed-circuit breathing device 10 generally includes a breathing port 12 in fluid communication with an expiratory limb 14 and an inspiratory limb 16, which collectively form a breathing circuit. As one example, the breathing port 12 can include a nose clip or a mask that covers the subject's face so as to prevent loss of gas through the subject's nose.

As will be described below in more detail, the expiratory limb 14 is generally configured to allow the expiration of gases, whether to atmosphere or an expiratory reservoir, while bringing the concentration of oxygen in the closed-circuit breathing device 10 to a predetermined value. In general, this predetermined value will depend on the desired concentration of xenon, or other therapeutic gas, and oxygen to be delivered to the subject during therapy. For example, if it is desired to have 25 percent oxygen, 25 percent xenon, and fifty percent nitrogen in a steady state, then prior to the delivery of Xe, the concentrations of O2 and N2 should be 33%(25/75) and 64% (50/74) respectively so that when the concentration of Xe is brought up to 25% the gases will be diluted maintaining their relative concentration difference. This is of course only a first approximation that needs to be refined depending on the relative volume of Xe to be absorbed by the subject's tissues, compared with the volume of N2 released from them. Generally, the solubility of both gases is small but somewhat greater for Xe than for Nitrogen. Thus the calculation of the estimated O2 and N2 prior to the Xe delivery may need to be adjusted to account for this effect, or the delivery of Xe may need to be incrementally adjusted after the estimated Xe concentration is reached.

Likewise, as will be described below in more detail, the inspiratory limb 16 is generally configured to allow the concentration of oxygen in the breathing circuit to reach a steady state while also gradually bringing the concentration of a therapeutic gas, such as xenon, into that steady-state by way of adding the therapeutic gas to the system in small, controlled volumes.

One-way valves, such as check valves 18 and 20, direct the flow of gas within the circuit in the direction from the inspiratory limb 16 to the expiratory limb 14 of the circuit. In some configurations, these check valves 18 and 20 and the breathing port 12 form a Hanz Rudolf valve 22.

A three-way valve 24 allows the expiratory limb 14 to exhaust to atmosphere or back into the closed circuit. Another three-way valve 26 allows the inspiratory limb 16 to receive air from atmosphere or, when not activated, gas from the rebreeding circuit 28. For safety, pop-in valve 30 and pop-out valve 32 allow inhalation and exhalation from room air if pressures are below −2 cm of water or above +2 cm of water, respectively.

The closed-circuit breathing device 10 is in fluid communication with an oxygen source. Preferably, the oxygen source is a source of 100 percent oxygen that is maintained at a controlled pressure, such as 10 bars. A demand valve 34 in the closed-circuit breathing device 10 is fed by the oxygen source. As one example, the demand valve 34 can be similar to those used in scuba diving systems. A small reduction of pressure in the breathing circuit will activate the demand valve 34 to deliver the required flow of oxygen to maintain the pressure above a minimal pressure.

The closed-circuit breathing device 10 is also in fluid communication with a therapeutic gas source. As one example, the therapeutic gas source can be a source of 100 percent xenon gas that is maintained at a controlled pressure, such as 10 bars. As another example, the therapeutic gas source can be a source of 80 percent xenon and 20 percent oxygen to ensure that a hypoxic mixture is never delivered into the breathing circuit. In other configurations, other therapeutic gases different from xenon can be used. In these configurations, the therapeutic gas sources can include 100 percent concentrations of the therapeutic gas, or can include mixtures of therapeutic gas with oxygen to ensure that a hypoxic mixture is not delivered into the breathing circuit.

In some configurations, the therapeutic gas source is coupled to the closed-circuit breathing device 10 by way of a solenoid normally open valve 36 to a small chamber 38 that has a known volume, $V_C$. The chamber 38 is coupled to the expiratory limb 14 of the breathing circuit by way of a solenoid normally closed valve 40. Activation of the solenoid valves 36 and 40 delivers a known volume of the therapeutic gas into the breathing circuit. To eliminate a failure mode where valves 40 and 36 are both in the open state, in some other configurations, the chamber 38 can be fed using a single two-way valve that when deactivated keeps the chamber 38 in connection to the pressurized source of therapeutic gas and when activated opens the chamber 38 to the breathing circuit. In this configuration, the solenoid valves 36 and 40 can thus be replaced with a single two-way valve.

In some other configurations, the therapeutic gas source can be coupled to the closed-circuit breathing device 10 by way of a mass-flow controller that delivers a flow of gas over a known time. The therapeutic gas source can also be coupled to the closed-circuit breathing device 10 by way of an orifice that is fed by a constant pressure that delivers the therapeutic gas at a known flow rate for an established time.

A soda lime reservoir 42 separates the expiratory limb 14 and the inspiratory limb 16 of the breathing circuit. As one example, the soda lime reservoir is shaped as an inverted pyramid to minimize the volume of soda lime. The soda lime reservoir 42 acts to absorb carbon dioxide, thereby removing the carbon dioxide from the breathing circuit.

The soda lime reservoir 42 is preferably enclosed in a thin-walled bag 44. The thin-walled bag 44 can expand, without increasing pressure, to a volume such that the thin-walled bag 44 can receive more than the maximum volume that the subject can exhale from total lung capacity ("TLC") to residual volume ("RV"), which is referred to as vital capacity ("VC").

Because xenon can leak across joints within the breathing circuit and across some materials, the closed-circuit breathing device 10 should be made of materials that minimize the loss of xenon, or other therapeutic gases, from the system. For example, the thin-walled bag 44 can be made of a highly gas-impermeable material, such as Mylar. Once the thin-walled bag 44 reaches its maximum capacity, the thin-walled bag 44 should become noncompliant.

The closed-circuit breathing device 10 also includes a sensor assembly 46 that is configured to measure the expiration of gases from the subject. Preferably, the sensor assembly 46 is in fluid communication with and distal to the breathing port 12, such that gases exhaled by the subject flow through the breathing port 12 and past the sensor assembly 46, where the volume, concentration, flow rate, and other properties of the exhaled gases can be measured.

In some configurations, the sensor assembly 46 can include a carbon dioxide ("CO2") sensor, a nitrogen sensor, a xenon sensor, an oxygen sensor, or combinations thereof. These sensors can be configured to measure the volume, concentration, flow rate, or combinations thereof, of the respective gas exhaled by the subject.

For example, the sensor assembly 46 can include a breathing gas flow meter with integrated CO2 sensor. This CO2 sensor allows for measurements of exhaled volume and CO2 concentration in real-time, and can provide an estimate of physiologic dead space volume ("VD").

As another example, the sensor assembly 46 can include gas analyzers for nitrogen, xenon, and oxygen. These gas analyzers sample the concentration of these gases on the conduit leading to the breathing port 12.

The closed-circuit breathing device may include a computer system 48 that interfaces with the closed-circuit breathing device 10 to provide control of the device and to receive measurements of data therefrom. For example, the computer system 48 can be in communication with the sensor assembly 46 to receive data from the sensors therein. The computer system 48 can also be in communication to activate the three-way valves 24 and 26, the solenoid valves 36 and 40 and programmed to control the closed-circuit breathing device 10.

The computer system 48 generally includes a display 50; one or more input devices 52, such as a keyboard and mouse; and a processor 54. The processor 54 may include a commercially available programmable machine running a commercially available operating system. The computer system 48 can provide an operator interface that enables control, operation, and monitoring of the closed-circuit breathing device 10.

In case of blockage in any part of the breathing circuit, or of failure of the demand valve 34 to deliver the required volume of oxygen to the subject, the pop-in and pop-out values 30 and 32 will open and allow the subject to safely breath from room air. The pressure at which pop-in valve 30 opens should be slightly more negative than the pressure that normally actuates the demand valve 34. The pressure at which the pop-out valve 32 opens should be slightly higher than the pressure required to move the expired gas flow across the soda lime reservoir 42 and the circuit elements up to the soda lime reservoir 42. In some configurations, a pressure sensor can be introduced in the closed-circuit breathing device 10 to alert the operator of any problems. The closed-circuit breathing device 10 is also configured to allow the subject to remove the breathing port 12 at any time.

The design of the closed-circuit breathing device 10 is such that the total volume of xenon, or other therapeutic gas, delivered to the subject is estimated based on patient measured parameters, and cannot be physically more than that selected by the user. This volume is independent of the xenon, or other therapeutic gas, sensor. Oxygen is delivered to replace that from metabolic use based on a mechanical system and independent of the sensors or computer calculations. However, should a system failure occur, an audible alarm can be sounded before the inhaled gas becomes hypoxic.

The computer system 48 can also be configured to continuously monitor oxygen concentrations measured by the sensor assembly 46. If the oxygen concentration falls below a safe level (e.g., 25%), an alarm can be generated and the computer system 48 can be operated to automatically open the system to atmosphere with the three-way valves 24 and 26.

In other configurations, the closed-circuit breathing device 10 can be operated without control by a computer system. For instance, the volume of therapeutic gas to be delivered to the breathing circuit can be estimated based on calculations and assumptions made before the breathing circuit is closed. As one example, the volume of therapeutic gas to deliver to the breathing circuit can be estimated based on the subject, based on the subject's age, height, sex, race, or other epidemiological factors, or combinations thereof.

Having described the general configuration of an example closed-circuit breathing device 10 in accordance with some configurations of the present disclosure, methods for operating and otherwise controlling such a device are now described.

Figure 2:
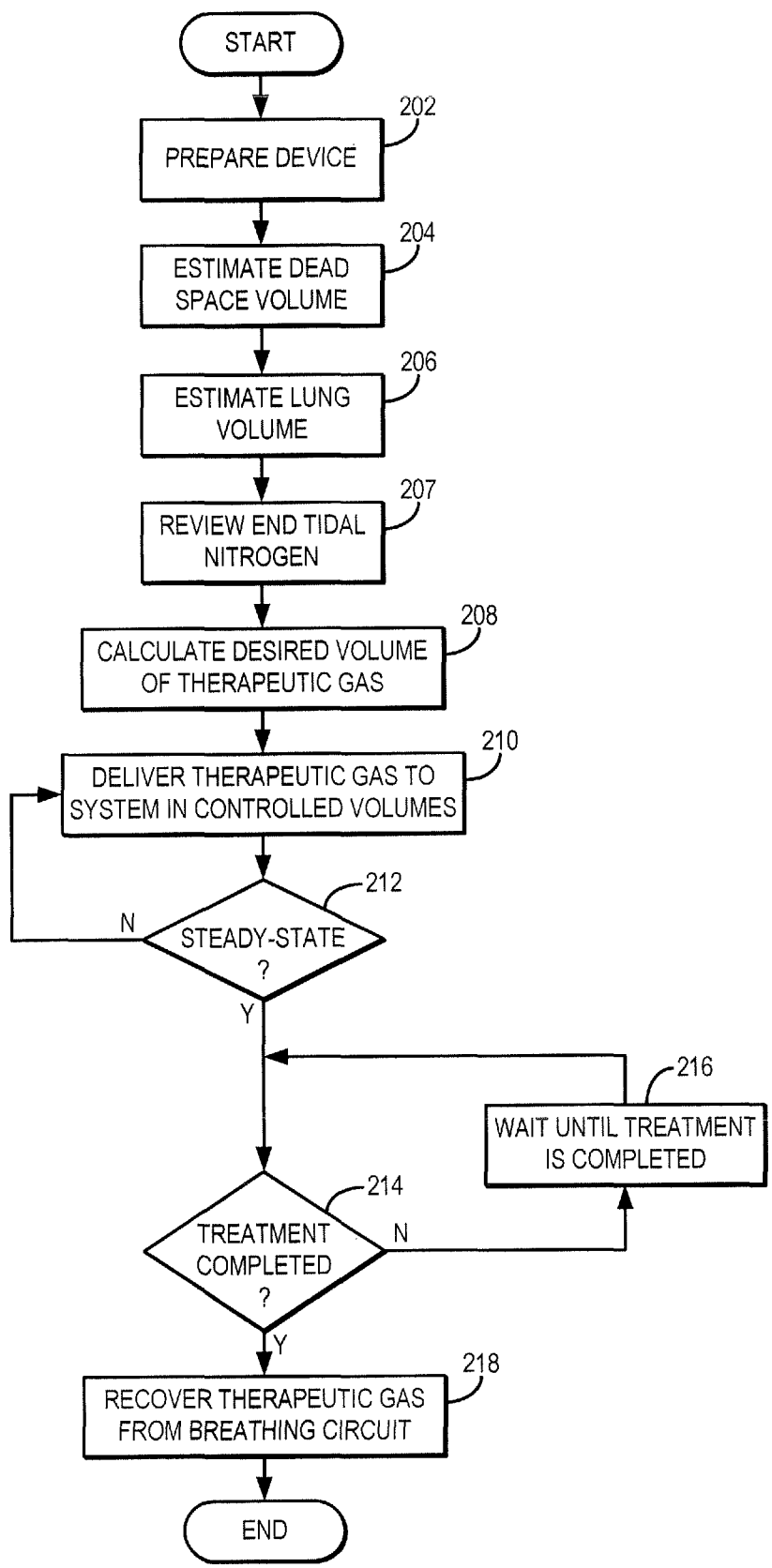
FIG. 2 is a flowchart setting forth the steps of an example method for operating a closed-circuit breathing device, such as the device shown in FIG. 1, to provide a therapeutic gas, such as xenon, to a subject in a steady-state equilibrium.

Referring now to FIG. 2, a flowchart is illustrated as setting forth the steps of an example method for operating a closed-circuit breathing device 10, such as the one described above. First, the breathing device is prepared, as indicated at step 202. Preparation of the device generally includes flushing the device with 100 percent oxygen and testing for leaks.

In one example, with the breathing port 12 closed, and the three-way valves 24 and 26 in their closed circuit positions, the demand valve 34 is manually activated to inflate the thin-walled bag 44 with 100 percent oxygen. The thin-walled bag 44 can be manually deflated by way of the pop-out valve 32. This process can be repeated to flush the soda lime reservoir 42 and conduits of the system with 100 percent oxygen. When the closed-circuit breathing device 10 has be adequately flushed with 100 percent oxygen in this manner, the three-way valves 24 and 26 can be placed in an open-circuit configuration.

With the three-way valves 24 and 26 in the open-circuit position, the subject is allowed to place the breathing port 12 on their mouth. Depending on the configuration of the breathing port 12, a nose clip may also be placed on the subject to prevent leaks and to the subject to become comfortable breathing through the mouth. As described above, in some configurations, the breathing port 12 can include a sealed mask that covers both the mouth and nose. At this point, the sensor assembly 46 is operated to estimate the subject's physiological dead space volume, $V_D$, as indicated at step 204. For example, the subject's physiological dead space volume can be measured from a plot of exhaled CO2 concentration versus volume concentration on each breath.

Next, the subject's lung volume, $V_L$, is estimated while the device is operated to washout nitrogen from the subject's lungs and from the breathing circuit, as indicated at step 206. For example, with three-way value 24 open to atmosphere, three-way valve 26 can be moved into a closed position. The subject will then inhale the 100 percent oxygen from the thin-walled bag 44 until its volume is exhausted. At this point, the demand valve 34 will supply the rest of the inhaled oxygen.

In this step, because the system should be flushed with 100 percent oxygen and the bag 44 empty, all inhaled gas will be 100 percent oxygen coming from the demand valve 34. During this period, the volume of the lung can be estimated from the breath-to-breath change in end tidal nitrogen concentration, the volume exhaled by the subject, and the anatomic dead space of the subject respiratory system estimated earlier. The subject's lung volume can also be estimated from a plot of the exhaled nitrogen concentration versus volume. The dead space volume can be used to more accurately estimate the lung volume from the nitrogen washout expirogram.

Exhalation sends expired gas flow through expiratory limb 14 to atmosphere by way of the three-way valve 24. As breathing continues with inspiratory gas at 100 percent oxygen concentration, nitrogen present in the subject's lung is washed out and expired oxygen concentration measured by the sensor assembly 46 increases.

As one example, mentioned above, the volume of the subject's lung, $V_L$, can be estimated after each breath, represented by the index, i, from the rate of nitrogen concentration, $F_{N2}$, during the washout of the gas as, $$V_L = (V_T - V_D)\frac{F_{N2(i+1)}}{F_{N2(i)} - F_{N2(i+1)}}; \quad (1)$$

where $V_T$ is the volume exhaled in each breath measured with a flow sensor in the sensor assembly 46 and $V_D$ is the dead space volume estimated from the sensor assembly 46. In some other configurations, the closed-circuit breathing device 10 can be configured to estimate the volume of the subject's lung, $V_L$, by calculating a breath-to-breath change in alveolar gas during the nitrogen washout.

The washout is allowed to progress until the end tidal nitrogen concentration reaches the desired value, $F_{N2}^*$, equal to, $$F_{N2}^* = 1 - F_{O2}^* - F_{Xe}^* \quad (2);$$

where $F_{O2}^*$ and $F_{Xe}^*$ are the target oxygen and xenon concentrations. It will be appreciated by those skilled in the art that if the therapeutic gas is a gas other than xenon, a suitable change can be made to Eqn. (2). After the washout period, the three-way valve 24 can be closed and the subject will be in re-breathing mode.

Thus, the closed-circuit breathing device 10 can be configured to allow inhalation of 100 percent oxygen and to washout nitrogen from the breathing circuit and the subject's body, to a desired level, before going into a closed, re-breathing mode.

Thus, at step 207, the end tidal nitrogen concentration is compared to a desired value to determine at least a drop in nitrogen equal to the concentration to be given of the therapeutic gas. If the concentration is higher, further washout breaths are conducted. Thus, the nitrogen washout period is used for both estimating the volume of the lungs, and for washing out the nitrogen to a concentration that, when adding the Xe to the circuit and using that volume of oxygen the oxygen concentration, will be higher or equal to that of room air. If not enough nitrogen is washout out as the oxygen is consumed by the subject, its concentration will become lower than that at room air (hypoxia).

As breathing continues, expired gas that has been scrubbed from CO2 is collected by the thin-walled bag 44. Because oxygen is consumed by the subject's body, the total volume of gas returning to the thin-walled bag 44 is less than the volume that needs to be inhaled in the subsequent breath. So, during inhalation the bag 44 will be emptied first, and at that time the pressure in the breathing circuit will become slightly negative, thereby triggering delivery of gas by the demand valve 34 to automatically supplement automatically the volume of oxygen consumed by the subject.

Based on the estimated volume of the subject's lung, $V_L$, and a measured value of the system volume, $V_S$, the volume of therapeutic gas, such as xenon, required to provide a desired concentration within the subject's lungs and the breathing system is calculated, as indicated at step 208. By way of example, the desired volume of xenon, or other therapeutic gas, can be calculated as follows:

$$V_{Xe} = (V_L + V_S + KV_{tissue}) \cdot F_{Xe}^* \quad (3);$$

where k is a xenon solubility constant, or a solubility constant for the therapeutic gas is the therapeutic gas is not xenon, and $V_{tissue}$ is an estimated volume of the tissues expected to absorb xenon or the other therapeutic gas. Xenon has a very low solubility in tissues and its absorption is minimal once a steady state is reached. As described here, because of this limited absorption, the volume of xenon that is needed to equilibrate the airspace (e.g., the lung and breathing circuit) can be estimated and rapidly delivered in a series of small boluses.

The initial concentration of xenon will generally be lower than the steady state concentration because, initially, there will be extra oxygen in the breathing system that will be consumed at a physiologic rate, thereby increasing the xenon concentration until the volume of the bag 44 is empty and oxygen starts to be taken from the demand valve 34. Because, during this time, some xenon will be taken from the airspace by blood and delivered to the rest of the body, its concentration may not increase as much, or may in fact remain constant, depending on the difference between oxygen consumption and xenon absorption (which will be small and reducing with time as the tissues equilibrate with the gas).

The therapeutic gas is then delivered to the breathing circuit in controlled volumes, $V_{Xe}$, as indicated at step 210. Because the volume of the chamber 38 is a known volume, $V_C$, and because the xenon or other therapeutic gas source is maintained at a controlled pressure, the volume of xenon or other therapeutic gas can be provided by pulsating the solenoid valves 36 and 40 n-number of times, where $$n = \frac{V_{Xe}}{P_{Xe} \cdot V_C}; \quad (4)$$

where $V_{Xe}$ is the desired volume of the xenon or other therapeutic gas, $P_{Xe}$ is the pressure of the xenon or other therapeutic gas source in atmospheres, and $V_C$ is the volume of the chamber 38. During delivery the concentrations of xenon and oxygen in the gases expired by the subject can be sensed by the sensor assembly 46 and monitored by computer software.

As the desired number xenon, or other therapeutic gas, "puffs" are delivered into the system, the concentration of xenon, $F_{Xe}$, or other therapeutic gas, will rise to a value lower than $F_{Xe}^*$ because of the additional volume introduced to the circuit. However, as the same volume of oxygen is consumed by the body, the value of $F_{Xe}$ will rise asymptotically to $F_{Xe}^*$ until the bag 44 at end inhalation is fully deflated. From there on, the demand valve 34 will provide the volume of oxygen consumed by the subject's body and the concentration of $F_{Xe}^*$ will be constant if its absorption rate by the subject's body has reached an equilibrium.

Once the breathing device reaches a steady-state equilibrium, the concentrations of xenon, oxygen, and nitrogen are expected to remain constant with minimal input from the computer during this phase. In this steady-state equilibrium, CO2 is absorbed by the soda lime, oxygen is provided automatically by the demand valve 34, and xenon should not be consumed or lost. However, if xenon continues to be absorbed by the tissues, or if it is lost out of the breathing circuit, its concentration will begin to drop and may need to be replenished in small aliquots over time following a determination that the steady state has been lost at decision block 212. When the breathing device has reached this steady-state equilibrium, it is maintained in that condition for the desired treatment time, as indicated by decision block 214. This treatment exposure time may be limited by the amount of CO2 that can be scrubbed by the soda lime reservoir 44.

The closed-circuit breathing device 10 and the methods for its use are designed to minimize the time of equilibration, but with enough damping to prevent overshoot or self sustained oscillations.

After the exposure time has elapsed, the re-breathed gases can be saved for recycling of the xenon, or other therapeutic gas, as indicated at step 218. For example, in some configurations, the closed-circuit breathing device 10 can be configured to recover the xenon, or other therapeutic gas, from the system by connecting the inhaled gas to 100 percent oxygen and the exhaled gas, after absorbing of the CO2, to a bag made of non-permeable material via three-way valve 26.

The closed-circuit breathing device described above can also be configured for a "digital" gas delivery method using a reservoir and either two 2-way valves or one 3-way valve. In such a configuration, xenon, or another therapeutic gas, is delivered in small increments of volume equal to the volume of chamber 38 times the pressure (in atmospheres) of the xenon, or other therapeutic gas, source:

$$V_{inc} = (P_C \cdot P_{Xe}) \quad (5).$$

The delivery rate of the xenon, or other therapeutic gas, in this instance equals the incremental volume, $V_{inc}$, time the number of deliveries per unit time.

In some configurations, the closed-circuit breathing device 10 can be configured for simplified use in home or in-the-field applications. In these scenarios, a number of breaths with 100 percent oxygen can be utilized to bring the breathing circuit's nitrogen concentration to a certain, estimated level before operating the closed0circuit breathing device 10 in a closed mode.

By way of example, in some of these configurations, after going into a closed mode, the closed-circuit breathing device 10 can be configured and operated to deliver a known volume of an oxygen diluted therapeutic gas into the breathing circuit based on the volume of the circuit and on an estimate of the subject's lung volume. As one example, the oxygen diluted therapeutic gas can include a mixture of 80 percent xenon and 20 percent oxygen. In these configurations, the estimate of the subject's lung volume can be made based on the subject's height, sex, race, or other epidemiological factors.

Thus, the systems and methods described here provide an advantageous xenon delivery mode in terms of cost, xenon utilization, ease of use, safety, and portability. The closed-circuit breathing device described here enables safe administration of xenon and other therapeutic gases to human subjects by non-specialists, in general clinical settings, and even possibly on demand by outpatients. This ease of use allows rapid treatment when symptoms of PTSD (fear/flashbacks), OCD (obsessions/compulsions), or addiction (drug high, cravings/urges, withdrawal effects) occur. Other disorders that could benefit from xenon self-administration include pain disorders/migraine and epilepsy/seizure disorders. It is anticipated that the closed-circuit breathing device described here can also be used to treat people with brain disorders involving similar biological targets.

The main design constraints of a human device for delivering xenon gas for therapy include safety, cost effectiveness, and accuracy. The systems and methods described here address safety by including tight control of breathing gas concentrations with redundant hardware/software safety features. The systems and methods described here address cost effectiveness by providing a commercial device that could include a disposable circuit, mouth-piece, filter, and CO2 absorber. Moreover, xenon, or other therapeutic gas, use is minimized by the circuit design and algorithms for smart gas delivery tailored to the individual user. The systems and methods described here address accuracy by providing a system capable of achieving a desired steady concentration of xenon, or another therapeutic gas, in a few minutes and maintained within tight bounds.

Figure 3:
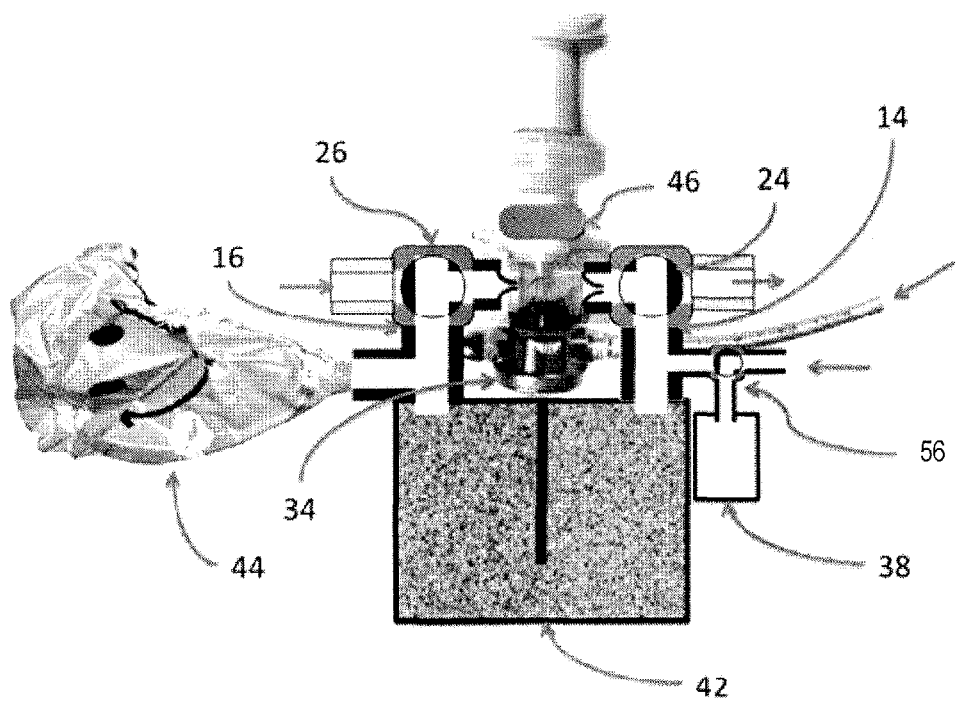
FIG. 3 is an example of another closed-circuit breathing device that can be used for the delivery of a therapeutic gas, such as xenon, to a subject with minimal loss of the therapeutic gas to the atmosphere, in which a commercial CO2 absorber is implemented.

Referring now to FIG. 3, in an alternative configuration the closed-circuit breathing device 10 can include a commercial CO2 absorber 42. In addition, this alternative configuration may not include pop-in valve 30 and pop-put valve 32. This configuration also makes use of a two-way solenoid valve 56 for introducing the therapeutic gas into the breathing circuit, as described above as an alternative to the dual solenoid valves 36 and 40.

Figure 4:
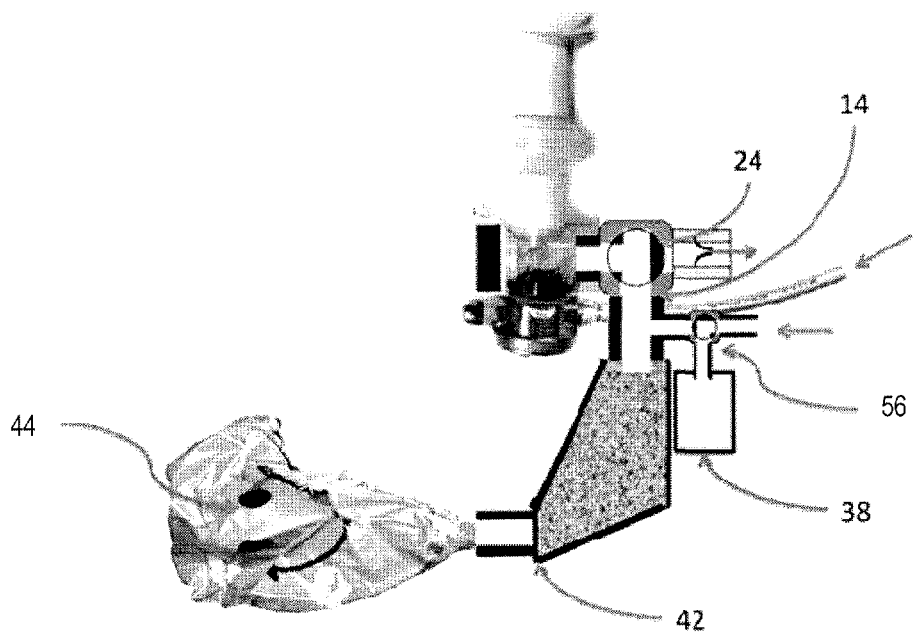
FIG. 4 is another example of a closed-circuit breathing device that can be used for the delivery of a therapeutic gas, such as xenon, to a subject with minimal loss of the therapeutic gas to the atmosphere, in which little to no gas sensors are used.

Referring now to FIG. 4, another alternative configuration of the closed-circuit breathing device 10 is illustrated. In this alternative design, can be operated with a reduced number of gas sensors, or with no sensor assembly at all. Instead of a full re-breathing circuit, the subject breathes in and out through the CO2 absorber 42. Before starting, the bag 44 could be filled until it has a known volume of oxygen. Initially, valve 24 is connecting the mouthpiece 12, the bag 44, and the exit to atmosphere such that the subject will inhale from the bag 44 and exhale out to atmosphere via a check valve until the bag 44 is empty. Breathing 100 percent oxygen from the bag with exhalation to atmosphere will result in a reduction in nitrogen to a desired level that will depend on the relative volumes of the lung and the initial bag volume. At this point the valve 24 can be rotated so that the subject will be inhaling from the demand valve 34 and exhaling into the bag. The initial volume of the bag 44 is chosen according to an estimated lung volume based on the size of the subject.

When three-way valve 24 is closed to atmosphere, because the bag 44 is empty. the subject will inhale from the demand valve 34 and exhale into the bag 44 in the first breath. During the following breaths, the demand valve 34 will only replenish the oxygen being consumed by the subject. At this point, a specified volume of xenon, or other therapeutic gas, is introduced into the system and a steady-state concentration of this gas is reached when the same volume of oxygen is consumed by the subject. The volume of xenon, or other therapeutic gas, is also based on the estimated size of the subject's lung volume. The steady-state concentrations of oxygen and xenon, or other therapeutic gas, will therefore depend on the accuracy of the volume estimates. It is contemplated that different systems could be designed for subjects of different sizes.

Alternatively, the inlet to valve 40 could be connected first to an oxygen tank to prefill the system with a known volume of oxygen, and later to the xenon, or other therapeutic gas, tank to introduce that gas. A microprocessor could then choose the volumes of each gas based on an estimated size of the subject and the desired steady-state concentrations.

Alternatively, the system could have an oxygen sensor sampling the exhaled air concentration. Instead of estimating a volume of oxygen to fill the bag 44, the valve 24 could be configured to couple the subject to atmosphere via a check valve. Each breath from the subject will then be inhaled from the demand valve 34 and exhaled to atmosphere through the check valve until the oxygen concentration of the exhaled gas is higher than a certain value, such that addition of a predetermined volume of xenon, or other therapeutic gas, will not make the breathing steady-state gas mixture hypoxic. At a point where the desired concentration of oxygen is reached, the valve 24 can be turned to connect the exhaled gas to the CO2 absorber. The first breath will come from bag 44 via the CO2 absorber and only the oxygen consumed by the subject will be provided by the demand valve 34 at the end of each breath.

In this configuration of the closed-circuit breathing device 10, the actual concentration of xenon, or other therapeutic gas, will be determined by the precision of the estimated lung volume. If the lung volume is underestimated, the concentration of xenon, or other therapeutic gas, will be higher than desired, or lower if the lung volume is overestimated. The utilization of this system therefore depends on relatively wide safety and therapeutic ranges of the xenon concentration and on the accuracy of the lung volume estimate.

Therefore, it is another aspect of the disclosure to provide a method for operating a closed-circuit breathing device having a breathing circuit. The method includes delivering oxygen to the breathing circuit to establish a predetermined concentration of oxygen in the breathing circuit while operating the closed-circuit breathing device in a closed configuration. A dead space volume, such as a dead space volume of the subject's airway, is estimated based on carbon dioxide exhaled into the breathing circuit during a washout period while operating the closed-circuit breathing device in an open configuration. In addition, the subject's lung volume is estimated based at least in part on the estimated dead space volume and on nitrogen exhaled into the breathing circuit during a washout period while operating the closed-circuit breathing device in an open configuration. For example, the subject's lung volume can be based in part on the volume of breathing gas and its nitrogen concentration that is exhaled during the washout period. The nitrogen washout period is conducted until the nitrogen concentration within the lung is reduced by a fraction equal or greater than the desired concentration of the therapeutic gas to be added. A volume of therapeutic gas to deliver to the breathing circuit is then estimated based at least in part on the estimated lung volume and the desired concentration of the therapeutic gas. The estimated volume of therapeutic gas is then introduced into the breathing circuit while operating the closed-circuit breathing device in a closed configuration. While operating the closed-circuit breathing device in a closed configuration, the closed-circuit breathing device is then controlled to maintain the concentrations of the therapeutic gas and oxygen in the breathing circuit at steady-state values for a treatment period.

The present invention has been described in terms of one or more preferred embodiments, and it should be appreciated that many equivalents, alternatives, variations, and modifications, aside from those expressly stated, are possible and within the scope of the invention.

The invention claimed is:
1. A closed-circuit breathing device, comprising:
a breathing port;
a breathing circuit in fluid communication with the breathing port;

a sensor assembly at a distal end of and in fluid communication with the breathing port, the sensor assembly being configured to measure at least one of a concentration or a flow rate of gases exhaled into the breathing circuit and including at least an oxygen sensor;

a chamber in fluid communication with the breathing circuit and configured to hold a known volume of a therapeutic gas;

a controller in communication with the sensor assembly and the chamber, the controller being configured to receive data from the sensor assembly and, based on the received data, to control delivery of the therapeutic gas from the chamber to bring a concentration of the therapeutic gas in the breathing circuit to a predetermined steady-state value with the breathing circuit in a closed-circuit configuration; and a first valve in fluid communication with an expiratory limb of the breathing circuit and a second valve within an inspiratory limb of the breathing circuit, wherein the sensor assembly receives the gases in the breathing circuit when the first valve and the second valve are in either an open-circuit configuration or a closed-circuit configuration.

2. The closed-circuit breathing device as recited in claim 1, wherein the sensor assembly includes a nitrogen sensor.

3. The closed-circuit breathing device as recited in claim 2, wherein the controller is configured to measure a concentration of nitrogen exhaled into the breathing circuit during a washout period and to estimate a volume of a subject's lungs therefrom.

4. The closed-circuit breathing device as recited in claim 1, further comprising a demand valve in fluid communication with the breathing circuit, the demand valve being configured to be coupled to an oxygen source so as to deliver oxygen to the breathing circuit in response to a pressure change in the breathing circuit.

5. The closed-circuit breathing device as recited in claim 1, further comprising a carbon dioxide absorber positioned between the inspiratory limb and the expiratory limb of the breathing circuit.

6. The closed-circuit breathing device as recited in claim 5, wherein the carbon dioxide absorber comprises a soda lime reservoir.

7. The closed-circuit breathing device as recited in claim 5, wherein the first valve is a three-way valve moveable between the open-circuit configuration to exhaust gases in the breathing circuit to the atmosphere and the closed-circuit configuration to circulate gases in the expiratory limb of the breathing circuit to the carbon dioxide absorber.

8. The closed-circuit breathing device as recited in claim 5, wherein the second valve is a three-way valve moveable between the open-circuit configuration to receive gases into the breathing circuit from the atmosphere and the closed-circuit configuration to circulate gases from the carbon dioxide absorber to the inspiratory limb of the breathing circuit.

9. The closed-circuit breathing device as recited in claim 5, further comprising a gas impermeable bag coupled to the breathing circuit and disposed about the carbon dioxide absorber, the gas impermeable bag being configured to store a volume of gas in the breathing circuit with minimal loss of the gas to the atmosphere.

10. The closed-circuit breathing device as recited in claim 1, wherein the sensor assembly includes a carbon dioxide sensor, and the controller is configured to estimate a dead space volume based on data received from the carbon dioxide sensor.

11. The closed-circuit breathing device as recited in claim 1, further comprising a pop-in valve in fluid communication with the breathing circuit and a pop-out valve in fluid communication with the breathing circuit, the pop-in valve being configured to open the breathing circuit to atmosphere when a pressure in the breathing circuit drops below a first pressure value and the pop-out valve being configured to open the breathing circuit to atmosphere when a pressure in the breathing circuit rises above a second pressure value.

12. A method for operating a closed-circuit breathing device having a breathing circuit, the steps of the method comprising:

(a) delivering oxygen to the breathing circuit to establish a predetermined concentration of oxygen in the breathing circuit while operating the closed-circuit breathing device with the absence of a therapeutic gas in the breathing circuit;

(b) estimating a dead space volume based on carbon dioxide exhaled into the breathing circuit during a washout period while operating the closed-circuit breathing device in an open configuration;

(c) estimating a lung volume based at least in part on the estimated dead space volume and on nitrogen exhaled into the breathing circuit during a washout period while operating the closed-circuit breathing device in the open configuration;

(d) estimating a volume of therapeutic gas to deliver to the breathing circuit based at least in part on the estimated lung volume;

(e) controlling the closed-circuit breathing device to maintain oxygen concentration in the breathing circuit at a steady-state value while raising a concentration of the therapeutic gas in the breathing circuit to a steady-state value while operating the closed-circuit breathing device in a closed configuration; and (f) controlling the closed-circuit breathing device to maintain the concentration of the therapeutic gas in the breathing circuit at the steady-state value for a treatment period while operating the closed-circuit breathing device in the closed configuration.

13. The method as recited in claim 12, wherein step (c) includes estimating the lung volume based on a volume of gas exhaled into the breathing circuit during a number of breaths, the estimated dead space volume, and a rate of nitrogen concentration change in the breathing circuit during the number of breaths.

14. The method as recited in claim 13, wherein step (c) includes estimating the lung volume during the washout period until an end tidal nitrogen concentration reaches a desired value.

15. The method as recited in claim 12, wherein step (d) includes estimating the volume of therapeutic gas to deliver to the breathing circuit based on the estimated lung volume, a measured volume of the breathing circuit, a solubility constant for the therapeutic gas, an estimated volume of tissues expected to absorb the therapeutic gas, and a target concentration of the therapeutic gas.

16. The method as recited in claim 12, wherein step (e) includes raising the concentration of the therapeutic gas in the breathing circuit to the steady-state value by delivering the therapeutic gas into the breathing circuit in controlled volumes equal to the estimated volume of therapeutic gas to deliver to the breathing circuit.

17. The method as recited in claim 16, wherein step (e) includes estimating a number of controlled volumes of therapeutic gas required to raise the concentration of the therapeutic gas in the breathing circuit to the steady-state value, the number of controlled volumes being estimated based at least in part on the estimated volume of therapeutic gas to deliver to the breathing circuit and a pressure of the therapeutic gas delivered to the breathing circuit.

18. The method as recited in claim 12, wherein the therapeutic gas is xenon.

19. The method as recited in claim 12, wherein the therapeutic gas is a mixture of oxygen and xenon.

20. The method as recited in claim 19, wherein the therapeutic gas is a mixture of 20 percent oxygen and 80 percent xenon.

21. The closed-circuit breathing device as recited in claim 1, wherein the controller is further configured to control the configurations of the first valve and the second valve.

22. The closed-circuit breathing device as recited in claim 1, further comprising:
- a first solenoid valve in fluid communication with the chamber, the first solenoid valve being configured to be coupled to a therapeutic gas source; and
- a second solenoid valve in fluid communication with the chamber and the expiratory limb of the breathing circuit,
- wherein pulsation of the first solenoid valve and the second solenoid valve is configured to deliver controlled volumes of the therapeutic gas into the breathing circuit.

* * * * *